(12) United States Patent
Lee et al.

(10) Patent No.: US 9,707,111 B2
(45) Date of Patent: Jul. 18, 2017

(54) STENT WITH OFFSET CELL GEOMETRY

(71) Applicant: Covidien LP, Mansfield, MA (US)

(72) Inventors: Nathan Lee, Golden Valley, MN (US); Paul Thompson, Minnetonka, MN (US)

(73) Assignee: Covidien LP, Mansfield, MA (US)

( * ) Notice: Subject to any disclaimer, the term of this patent is extended or adjusted under 35 U.S.C. 154(b) by 197 days.

(21) Appl. No.: 14/501,265

(22) Filed: Sep. 30, 2014

(65) Prior Publication Data

US 2015/0105853 A1   Apr. 16, 2015

Related U.S. Application Data

(63) Continuation of application No. 13/175,015, filed on Jul. 1, 2011, now Pat. No. 8,876,888, which is a continuation of application No. 11/950,931, filed on Dec. 5, 2007, now Pat. No. 7,993,388, which is a continuation of application No. 09/955,351, filed on Sep. 17, 2001, now abandoned.

(51) Int. Cl.
  *A61F 2/06* (2013.01)
  *A61F 2/915* (2013.01)
  *A61F 2/91* (2013.01)

(52) U.S. Cl.
  CPC .............. *A61F 2/915* (2013.01); *A61F 2/91* (2013.01); *A61F 2002/91508* (2013.01); *A61F 2002/91533* (2013.01); *A61F 2002/91558* (2013.01); *A61F 2002/91583* (2013.01)

(58) Field of Classification Search
  CPC .. A61F 2/915; A61F 2/91; A61F 2002/91558; A61F 2002/91508; A61F 2002/91583; A61F 2002/91533
  See application file for complete search history.

(56) References Cited

U.S. PATENT DOCUMENTS

| | | |
|---|---|---|
| 5,449,373 A | 9/1995 | Pinchasik et al. |
| 5,514,154 A | 5/1996 | Lau et al. |
| 5,824,059 A | 10/1998 | Wijay |
| 6,033,433 A | 3/2000 | Ehr et al. |
| 6,066,167 A | 5/2000 | Lau et al. |
| 6,129,755 A | 10/2000 | Mathis et al. |
| 6,132,460 A | 10/2000 | Thompson |
| 6,132,461 A | 10/2000 | Thompson |
| 6,190,406 B1 | 2/2001 | Duerig et al. |

(Continued)

FOREIGN PATENT DOCUMENTS

| | | |
|---|---|---|
| EP | 0928605 A2 | 7/1999 |
| EP | 0928605 A3 | 3/2000 |

(Continued)

OTHER PUBLICATIONS

Prosecution History from U.S. Appl. No. 09/955,351, dated from Nov. 21, 2003 through Feb. 6, 2007, 44 pp.

(Continued)

*Primary Examiner* — Julian W Woo

(57) ABSTRACT

A stent defining a longitudinal axis is disclosed. A plurality of circumferential support structures are spaced-apart along the longitudinal axis. At least some of the circumferential support structures are interconnected by connection members that extend generally in a circumferential direction.

15 Claims, 9 Drawing Sheets

(56) References Cited

U.S. PATENT DOCUMENTS

| | | |
|---|---|---|
| 6,231,598 B1 * | 5/2001 | Berry .................. A61L 31/022 |
| | | 623/1.15 |
| 6,241,760 B1 | 6/2001 | Jang |
| 6,264,687 B1 * | 7/2001 | Tomonto ................. A61F 2/91 |
| | | 623/1.16 |
| 6,340,366 B2 | 1/2002 | Wijay |
| 6,652,579 B1 * | 11/2003 | Cox ........................ A61F 2/91 |
| | | 623/1.15 |
| 6,776,793 B2 | 8/2004 | Brown et al. |
| 7,993,388 B2 | 8/2011 | Lee et al. |
| 8,114,146 B2 * | 2/2012 | Brown ..................... A61F 2/91 |
| | | 606/108 |
| 8,876,888 B2 | 11/2014 | Lee et al. |
| 2001/0047199 A1 | 11/2001 | Wijay |
| 2002/0156524 A1 | 10/2002 | Ehr et al. |
| 2003/0055485 A1 | 3/2003 | Thompson et al. |
| 2003/0167084 A1 | 9/2003 | Orlowski |

FOREIGN PATENT DOCUMENTS

| | | |
|---|---|---|
| EP | 1159934 A2 | 12/2001 |
| EP | 1049421 B1 | 1/2005 |
| WO | 95/31945 A1 | 11/1995 |
| WO | 96/26689 A1 | 9/1996 |
| WO | 97/40783 A3 | 11/1997 |
| WO | 98/40035 A1 | 9/1998 |
| WO | 0030563 A1 | 6/2000 |
| WO | 0101888 A1 | 1/2001 |

OTHER PUBLICATIONS

Prosecution History from U.S. Appl. No. 11/950,931, dated from Dec. 9, 2010 through Apr. 1, 2011, 16 pp.

Prosecution History from U.S. Appl. No. 13/175,015, dated from Apr. 11, 2014 through Jun. 30, 2014, 20 pp.

* cited by examiner

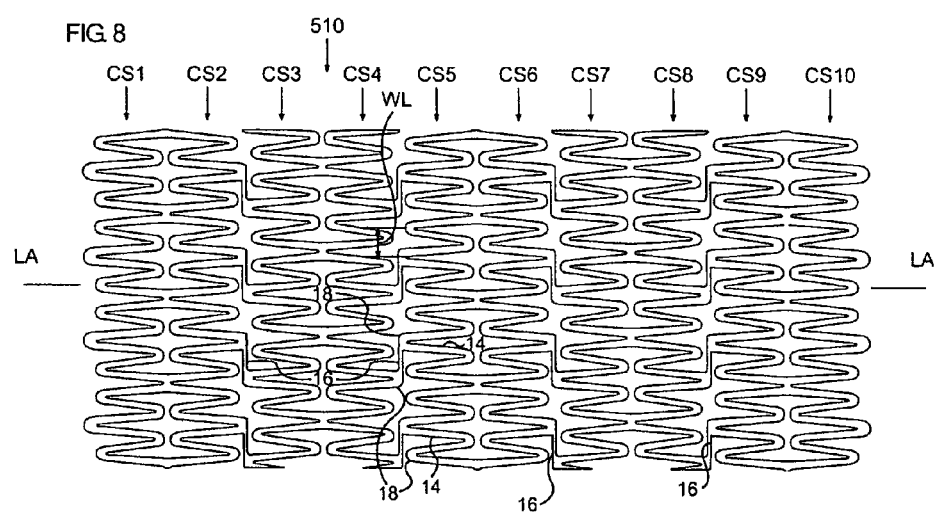

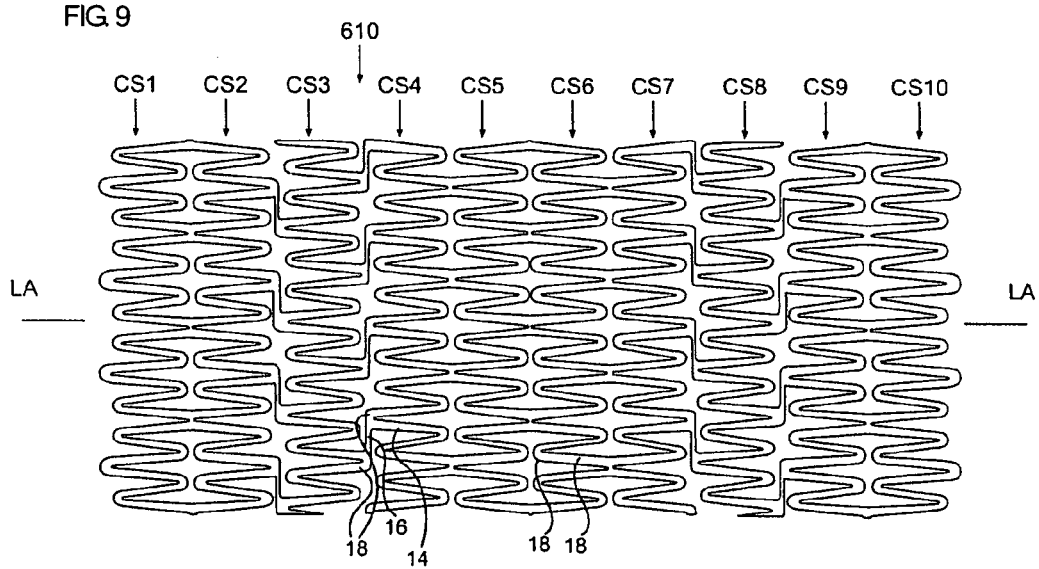

STENT WITH OFFSET CELL GEOMETRY

CROSS-REFERENCE TO RELATED APPLICATIONS

The present application is a continuation of U.S. patent application Ser. No. 13/175,015, entitled Stent with Offset Cell Geometry, filed Jul. 1, 2011, which is a continuation of U.S. patent application Ser. No. 11/950,931, filed Dec. 5, 2007, entitled Stent with Offset Cell Geometry, which is a continuation of U.S. patent application Ser. No. 09/955,351, entitled Stent with Offset Cell Geometry, filed Sep. 17, 2001, the complete disclosure of each of which are incorporated herein by reference for all purposes.

BACKGROUND OF THE INVENTION

1. Field of the Invention

This invention pertains to implants for use in intraluminal applications. More particularly, this invention pertains to stents for use in vascular applications.

2. Description of the Prior Art

Stents are widely used for supporting a lumen structure in a patient's body. For example, stents may be used to maintain patency of a coronary artery, other blood vessel or other body lumen.

Commonly, stents are metal, tubular structures. Stents are passed through the body lumen in a collapsed state. At the point of an obstruction or other deployment site in a body lumen, the stent is expanded to an expanded diameter to support the lumen at the deployment site.

In certain designs, stents are open-celled tubes that are expanded by inflatable balloons at the deployment site. This type of stent is often referred to as a "balloon expandable" stent and is often made of a plastically deformable material such as stainless steel. Other stents are so-called "self-expanding" stents. Self-expanding stents do not use balloons to cause the expansion of the stent. An example of a self-expanding stent is a tube (e.g., a coil tube or an open-cell tube) made of an elastically deformable material. Elastically deformable self-expanding stents are typically secured to a stent delivery device under tension in a collapsed state. At the deployment site, the stent is released so that internal tension within the stent causes the steal to self-expand to its enlarged diameter. This type of stent is often made of a "super-elastic" material such as nitinol. Other self-expanding stents are made of so-called shape-memory metals. Such shape-memory stents experience a phase change at the elevated temperature of the human body. The phase change results in expansion from a collapsed state to an enlarged state.

SUMMARY OF THE INVENTION

One embodiment of the present invention relates to a stent having a longitudinal axis. A plurality of circumferential support structures are spaced-apart along the longitudinal axis. At least some of the circumferential support structures are interconnected by connection members that extend generally in a circumferential direction.

A variety of advantages of the invention will be set forth in part in the description that follows, and in part will be apparent from the description, or may be learned by practicing the invention. It is to be understood that both the foregoing general description and the following detailed description are exemplary and explanatory only and are not restricted.

BRIEF DESCRIPTION OF THE DRAWINGS

FIG. 8 is a plan view of another embodiment of a stent according to the present invention, as it would appear if it were longitudinally split and laid out flat.

FIG. 9 is a plan view of another embodiment of a stent according to the present invention, as it would appear if it were longitudinally split and laid out flat.

Figure 1:
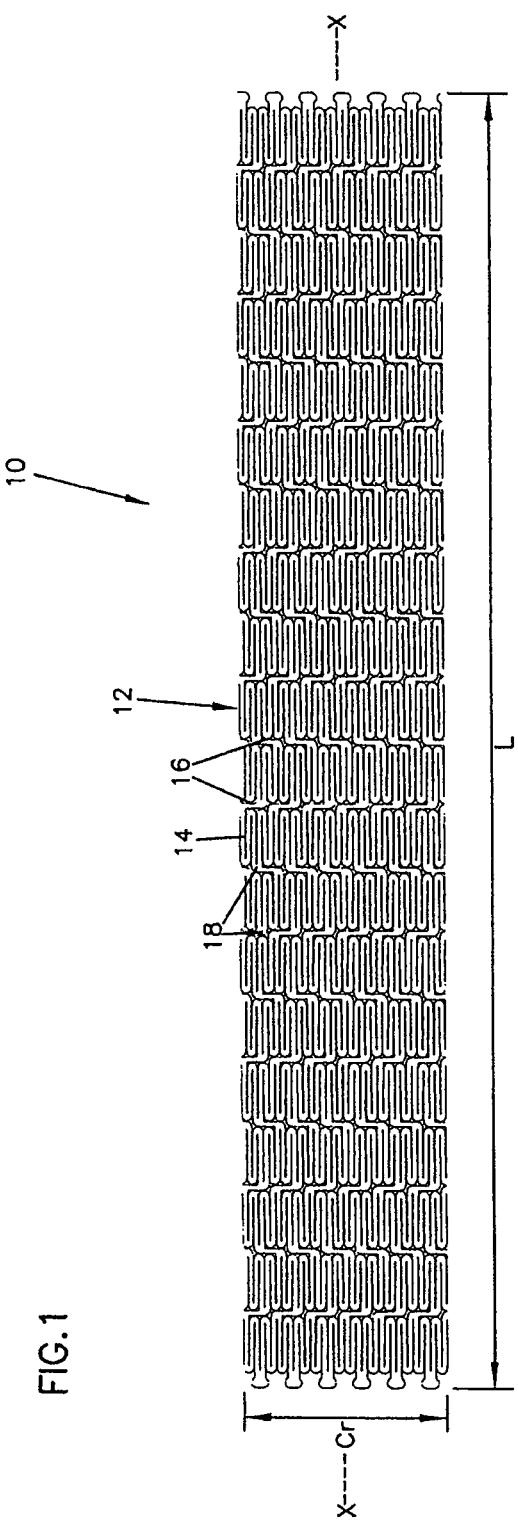
FIG. 1 is a plan view of a first embodiment of a stent according to the present invention as it would appear if it were longitudinally split and laid out flat.

While the invention is amenable to various modifications and alternative forms, the specifics thereof have been shown by way of example in the drawings and will be described in detail below. It is to be understood, however, that the intention is not to limit the invention to the particular embodiments described. On the contrary, the invention is intended to cover all modifications, equivalents and alternatives falling within the scope of the invention as defined by the appended claims.

DESCRIPTION OF THE ILLUSTRATED EMBODIMENTS

Referring now to the several drawing figures in which identical elements are numbered identically, a description of the preferred embodiment of the present invention will now be provided. In the following detailed description, references are made to the accompanying drawings that depict various embodiments in which the invention may be practiced. It is to be understood that other embodiments may be utilized, and structural and functional changes may be made without departing from the scope of the present invention. Further, each of the features disclosed herein can be considered stand-alone inventive features or features that have inventive aspects when considered in combination with one another.

Figure 6:
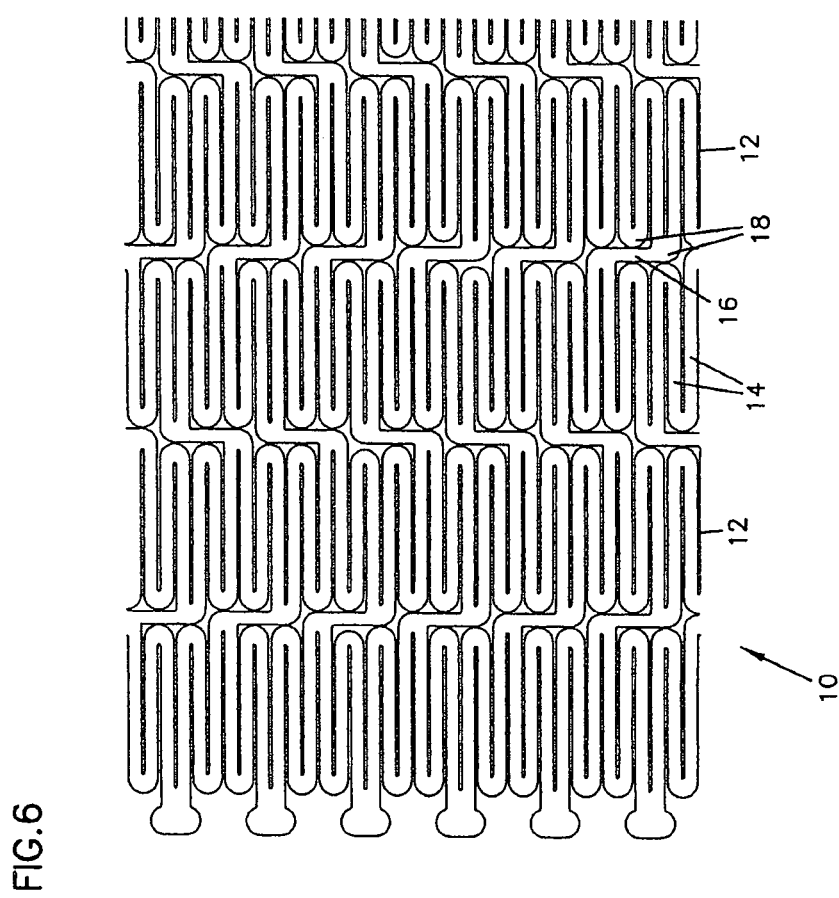
FIG. 6 is an enlarged partial view of the stent of FIG. 1.

FIG. 1 illustrates a stent 10, shown longitudinally split and laid flat, having an un-deployed or reduced circumference $C_r$ and an un-deployed length L. FIG. 6 is an enlarged partial view of FIG. 1 to better illustrate a strut geometry as will be described.

Figure 2:
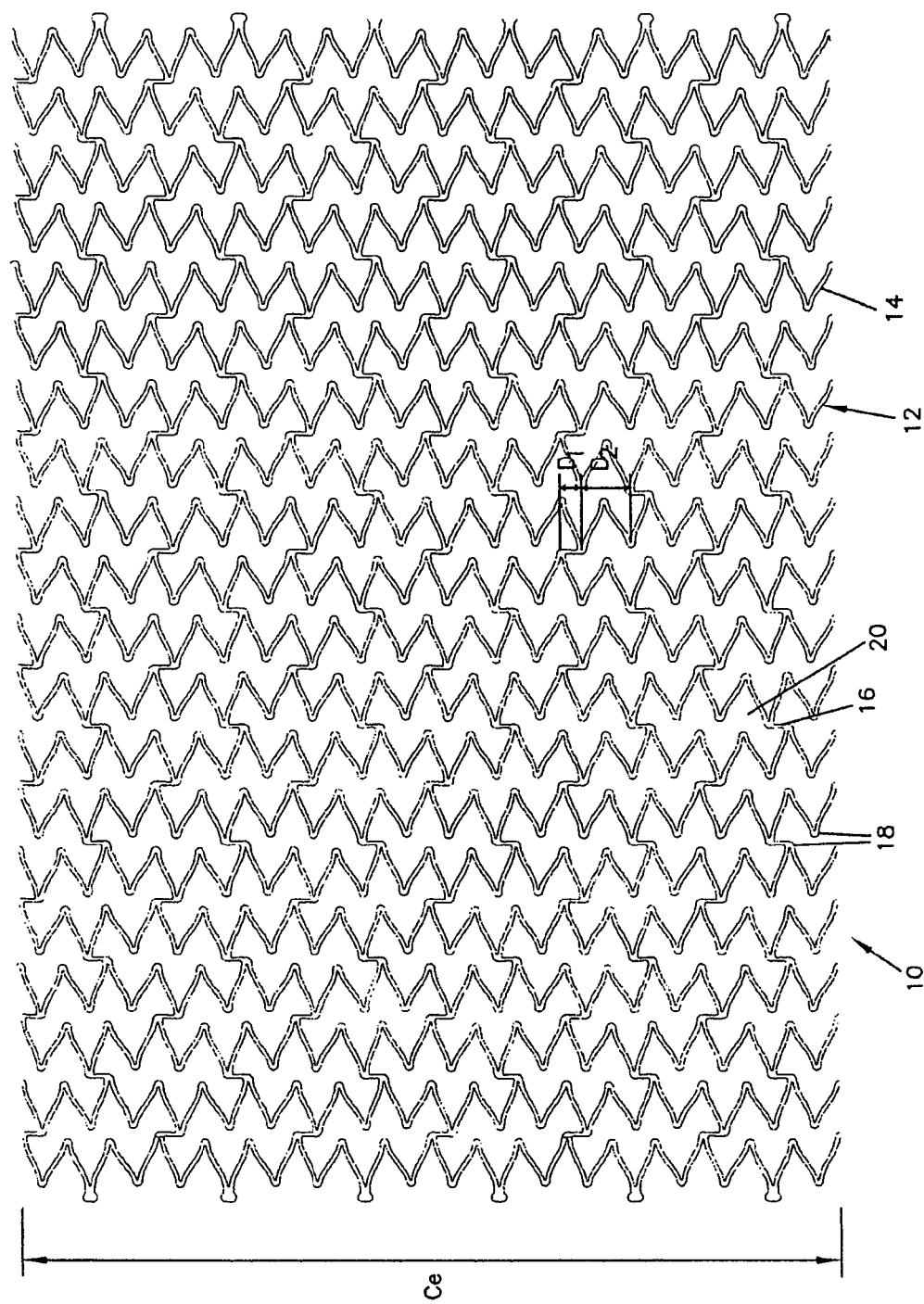
FIG. 2 is the view of FIG. 1 following expansion of the stent.

The stent 10 is a reticulated, hollow tube. The stent 10 may be expanded from the reduced circumference $C_r$ to an expanded or enlarged circumference $C_e$. FIG. 2 is a view illustrating the expanded stent 10 as it would appear if longitudinally split and laid flat. The enlarged circumference $C_e$ is shown in FIG. 2.

The material of the stent 10 defines a plurality of circumferential support structures 12 spaced apart along the longitudinal axis, X-X of the stent 10. The phrase "circumferential support structures" will be understood to include structures that extend generally about the circumference of the stent 10. The support structures 12 are formed by longitudinal struts 14. In one embodiment, the struts 14 have uniform cross-sectional dimensions throughout their length. Adjacent struts 14 within a support structure 12 are connected at apex portions 18 to form an undulating pattern that extends about the circumference of the stent 10. As used herein, "apex portion" is intended to mean the region where two struts 14 are joined. The apex portions 18 can be semi-circular, arcuate, pointed, square, oval, or any other shape. Adjacent support structures 12 are joined by circumferential connecting struts 16 joining apex portions 18. The phrase "circumferential connecting struts" or "circumferential connecting members" will be understood to mean struts or members that interconnect adjacent circumferential support structures 12 and have a spacial component or vector that extends in a circumferential direction about the stent 12. The struts 14, apex portions 18 and connecting struts 16 form bounded areas, or cells 20, which are open as shown in FIG. 2 (i.e., extend through the wall thickness of the stent 10).

The struts 14 may all be the same length, or they may be of differing length. In one embodiment, when some longer struts are present, the longer struts in adjacent support structures interconnected.

The stent 10 may be formed through any suitable means including laser or chemical milling. In such processes, a hollow cylindrical tube laser cut or etched to remove material and form the open cells 20.

Figure 7:
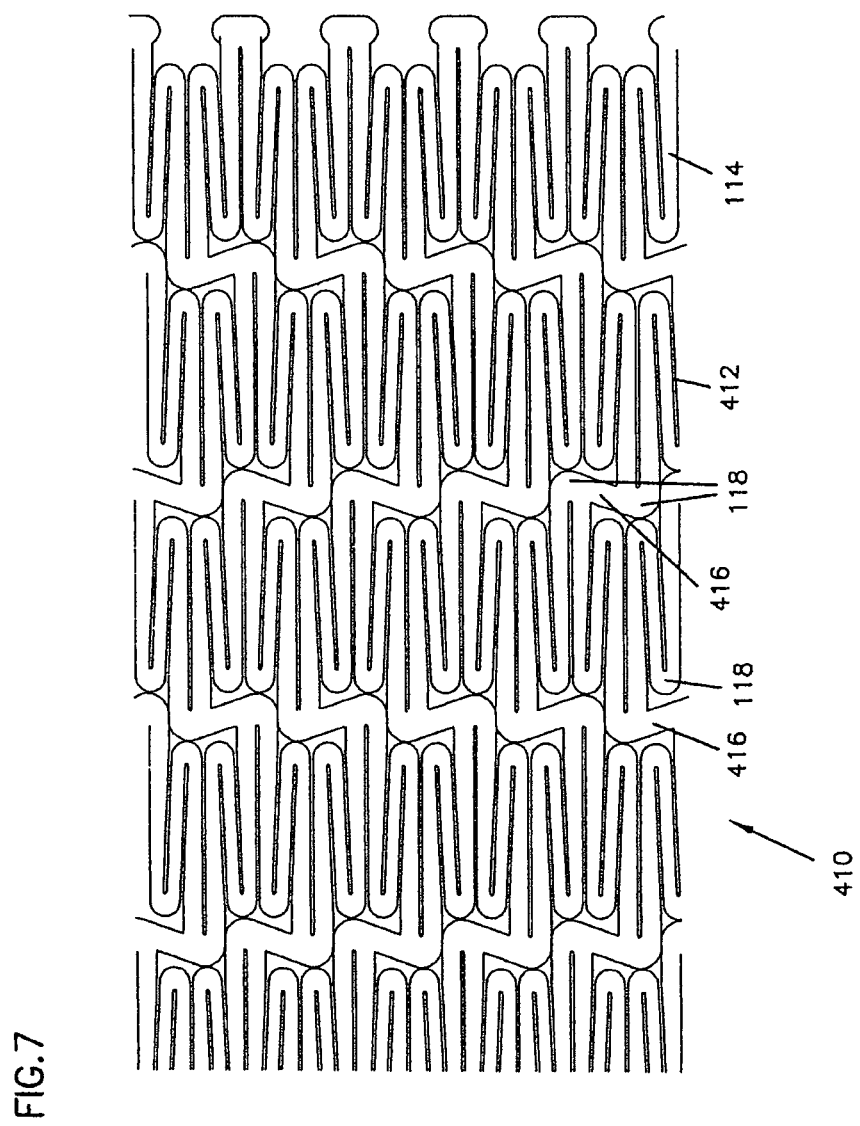
FIG. 7 is a partial plan view of another embodiment of a stent according to the present invention, as it would appear if it were longitudinally split and laid out flat.

In the embodiment of FIG. 1, the struts 14 extend along the longitudinal axis of the stent in the un-deployed orientation (FIGS. 1 and 6). At least some of the apex portions 18 are configured such that, when the stent is in the un-deployed orientation, they overlap in the axial/longitudinal direction. As used herein, "overlap" is intended to mean the apex portions 18 are directly in line circumferentially or the apex portions 18 extend past each other such that the connecting strut joining them is positioned at an angle relative to the circumference. In the embodiment illustrated in FIGS. 1 and 6, the overlapping apex portions 18 are directly in line circumferentially, and the connecting struts 16 are substantially perpendicular to the struts 14. In the embodiment illustrated in FIG. 7, apex portions 118 extending past each other are joined by angled connecting struts 416. The angled connecting struts 416 extend at an oblique angle with respect to the circumferential direction.

Figure 3:
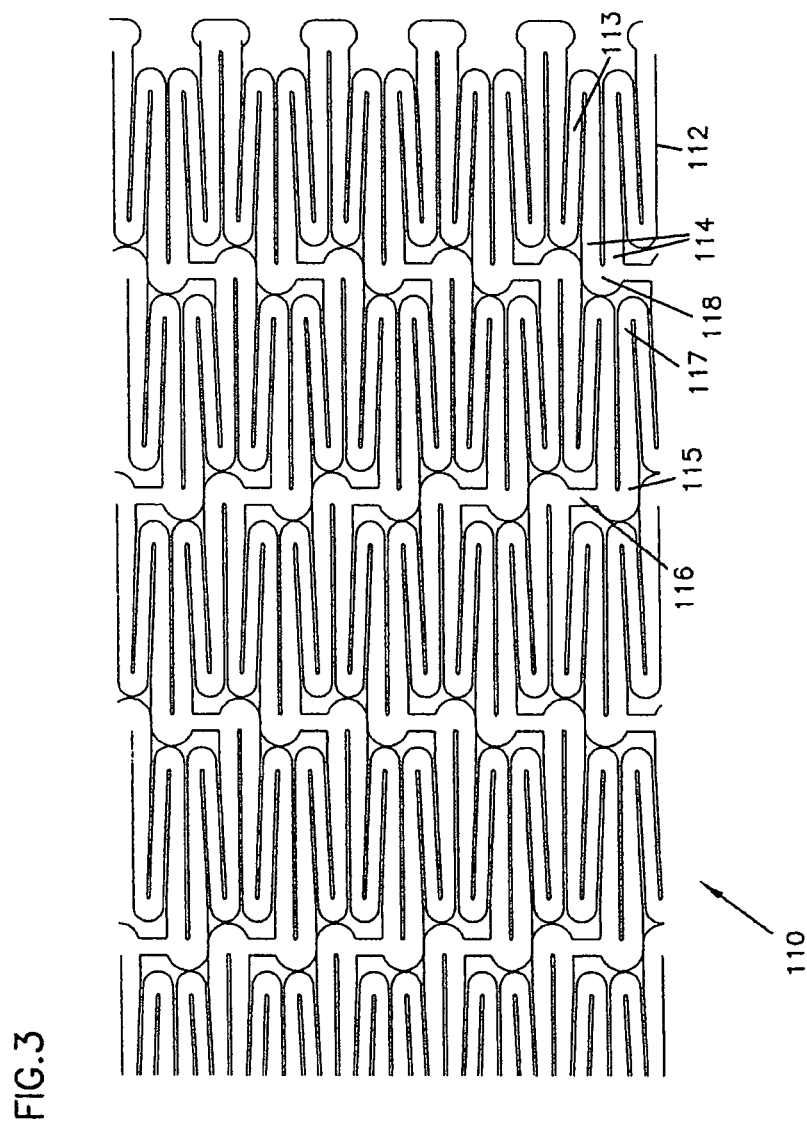
FIG. 3 is a partial plan view of a tapered-strut stent according to the present invention as it would appear if it were longitudinally split and laid out flat.

The embodiment of FIG. 3 includes longitudinal struts 114 that are tapered, as disclosed in co-pending, commonly assigned, U.S. patent application Ser. No. 09/765,725, the entire disclosure of which is incorporated herein by reference. In the embodiment illustrated in FIG. 3, circumferential support structures 112 are made up of pairs of tapered struts 114 alternating with single, non-tapered struts 113. The tapered struts 114 are arranged such that their wide ends 115 are adjacent circumferential connecting struts 116 and their narrow ends 117 are adjacent unconnected or free apex portions. In a further embodiment, the connecting struts 116 can connect only apex portions 118 joining narrow ends 117.

Figure 4:
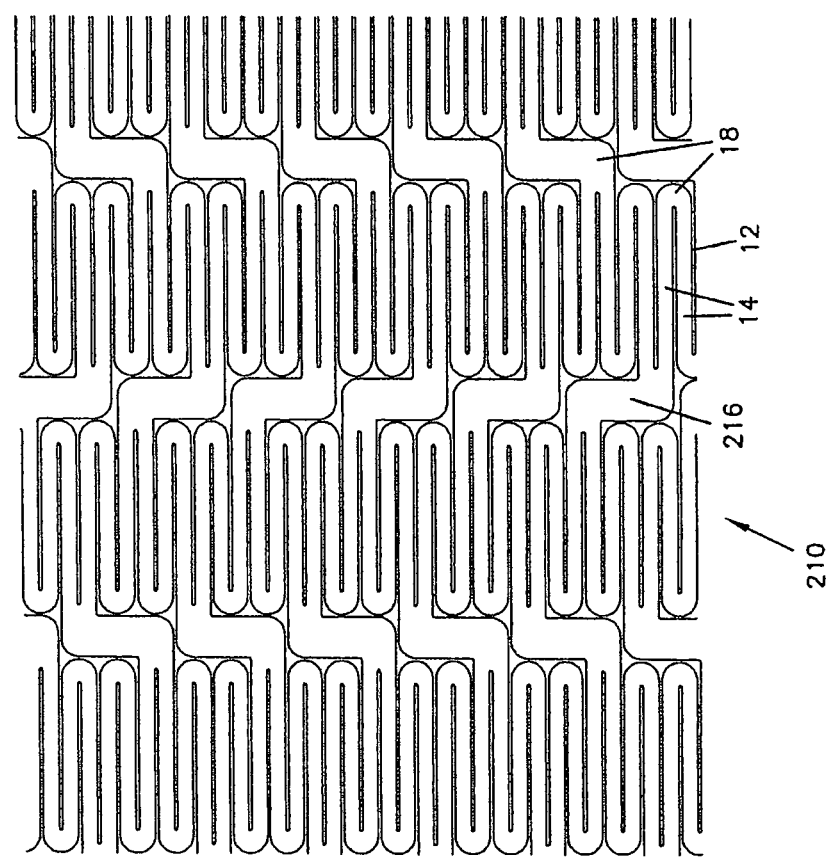
FIG. 4 is a partial plan view of another embodiment of a stent according to the present invention as it would appear if it were longitudinally split and laid out flat.
Figure 5:
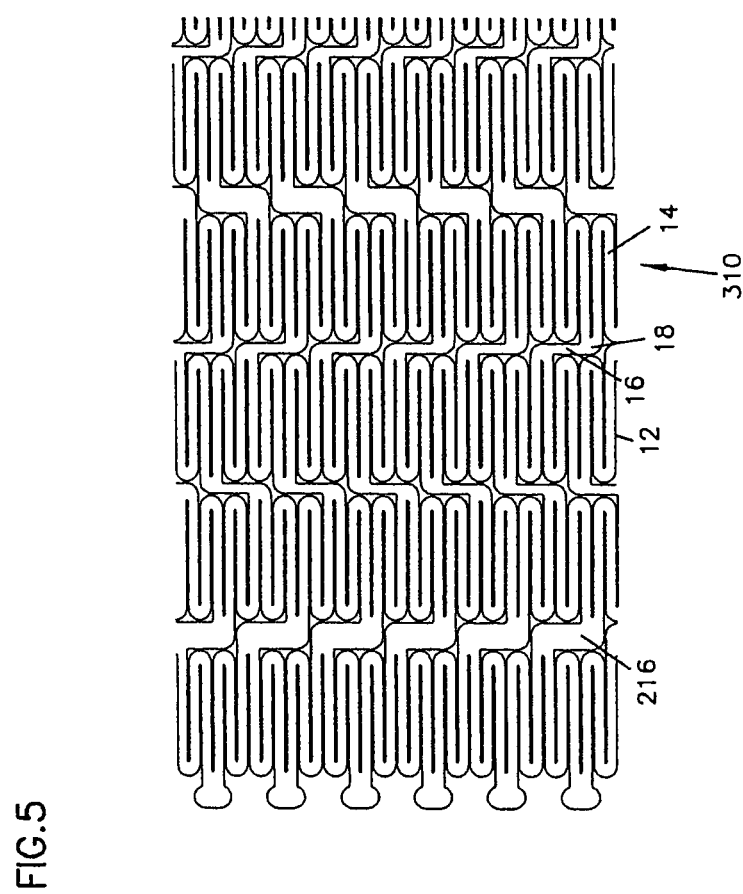
FIG. 5 is a partial plan view of another embodiment of a stent according to the present invention as it would appear if it were longitudinally split and laid out flat.

To increase the radiopacity of the stent, one or more of the connecting struts can have a width greater than the width of the longitudinal struts 14. In the embodiment illustrated in FIG. 4, all connecting struts 216 are wide. Preferably, the connecting struts 216 are at least 1.25, or 2, or 3, or 4, or 5, or 6, or 7 or 8 times as wide as the struts 14. By way of example, the connecting struts might range from 0.1 inch to 0.050 inches in width. In the embodiment illustrated in FIG. 5, wide connecting struts 216 are positioned between some of the support structures 12, and narrower connecting struts 16 are positioned between the remaining support structures 12. Incorporating both wide connecting struts 216 and narrower connecting struts 16 in the stent can provide a customized radiopacity.

In use, the stent 10 is advanced to a site in a lumen (e.g., an occlusion site in need of circumferential support) while in the compressed orientation. The stent 10 is then expanded at the site. The stent 10 may be expanded through any conventional means. For example, the stent 10 in the reduced diameter may be placed at the tip of a balloon catheter. At the site, the stent is expanded (e.g., through expansion of the balloon) thereby causing the stent to expand from the compressed orientation to the deployed orientation. A preferred material for balloon expandable stents is stainless steel. For self-expanding stents, the stent 10 may be formed of a super-elastic or shape memory material, such as nitinol, which is an alloy of nickel and titanium.

During expansion of the stent 10, the cells 20 open to a configuration as shown in FIG. 2. The expansion of the stent 10 is typically provided primarily through bending of the apex portions 18.

The stent 10 is highly flexible. To advance to a site, the axis X-X of the stent 10 bends to navigate through a curved lumen. Further, for placement at a curved site in a lumen, the stent 10 is preferably sufficiently flexible to retain a curved shape following expansion and to bend as the lumen bends over time. The stent 10, as described above, achieves these objections.

When bending on its axis X-X, the stent 10 tends to axially compress on the inside of the bend and axially expand on the outside of the bend. The present design permits such axial expansion and contraction. The cell geometry results in a structure that is highly flexible before and after radial expansion.

When the stent 10 is in the deployed orientation, as shown in FIG. 2, the apex portions 18 on adjacent support structures 12 are offset. When the stent 10 flexes and bends, the apex portions 18 and corresponding struts 14 on one support structure 12 do not come in direct contact with facing apex portions 18 and struts 14 on an adjacent support structure 12. This offset geometry provides increased flexibility to the stent 10 and allows the stent 10 to better conform to a lumen such as a coronary vessel.

In one embodiment, as shown in FIG. 2, the distance of offset $D_1$ provided by the connection member 16 is about one-half the distance $D_2$ provided between the apex portions 18 (i.e., $D_1=0.5D_2$). Thus, adjacent circumferential support structures 12 define waves that are "in-phase" with one another. This provides a greater longitudinal spacing (i.e., in a direction corresponding to the longitudinal axis of the stent) between the peaks as compared to having the apexes being in direct opposition to one another.

Table 1 provides examples of stent diameters and examples of offset geometry based on the number of apex portions around the circumference of the stent. It is to be understood that the dimensions in Table 1 are exemplary only and are not intended to be limiting. The dimensions are applicable to a stent in the expanded or deployed orientation. The stent dimensions will be selected based on the size and location of the lumen into which the stent is to be placed. This offset geometry allows for flexion of the stent without adjacent struts directly impacting each other. The preferred geometry has the apexes of struts in one support structure in between the apexes of struts in the adjacent support structure. When the stent is flexed, the apexes pass by one another and do not impact, which allows for increased flexibility.

TABLE I

| I.D. Diameter (mm) | I.D. Diameter (inch) | Circumference (inch) | Number of apexes around Circumference | Distance between apexes around Circumference (inch) | Preferred Offset: ½ distance between apexes around Circumference (inch) |
| --- | --- | --- | --- | --- | --- |
| 6.25 | 0.246 | 0.773 | 18 | 0.043 | 0.021 |
| 7.25 | 0.285 | 0.897 | 18 | 0.050 | 0.025 |
| 8.25 | 0.325 | 1.020 | 18 | 0.057 | 0.028 |
| 9.25 | 0.364 | 1.144 | 18 | 0.064 | 0.032 |

Numerous modifications are possible. For example the stent 10 may be lined with either an inner or outer sleeve (such as polyester fabric or ePTFE) for tissue growth. Also, the stent may be coated with radiopaque coatings such as platinum, gold, tungsten or tantalum. In addition to materials previously discussed, the stent may be formed of any one of a wide variety of previous known materials including, without limitation, MP35N, tantalum, platinum, gold, Elgiloy and Phynox.

While twenty support structures 12 are shown in FIGS. 1 and 2 connected and spaced apart along the longitudinal axis of the stent, a different number could be so connected to vary the properties of the stent 10 as a designer may elect. Likewise, while each support structure 12 in FIGS. 1 and 2 is shown as having 36 struts 14, the number of struts 14 could vary to adjust the properties of the stent. Also, while each support structure 12 is shown connected to an adjacent support structure 12 by 6 connecting struts 16, the number of connecting struts 16 could vary. In one embodiment, the stent is made up of 20 support structures, 36 struts per support structure, 18 apex portions on each side of each support structure, and 6 connecting struts joining every third apex portion of adjacent support structures. Alternating the direction of the connecting struts between support structures prevents uneven expansion angles between the struts and prevents twisting of the stent. For example, in FIG. 1, connecting struts 16 extend from one apex portion 18 down to another apex portion 18 between first and second support structures, and extend up between the second and third support structures. This alternating pattern of connecting struts is more pronounced in the embodiment with angled connecting struts 416, shown in FIG. 7.

When forming the stent from shape memory metal such as nitinol, the stent can be laser cut from a nitinol tube. Thereafter, the stent can be subjected to a shape-setting process in which the cut tube is expanded on a mandrel and then heated. Multiple expansion and heating cycles can be used to shape-set the stent to the final expanded diameter.

In use, the finished stent can be mounted on a delivery catheter. As is conventionally known in the art, the stent can be held in a compressed orientation on the delivery catheter by a retractable sheath. As is also known in the art, the delivery catheter can be used to advance the stent to a deployment location (e.g., a constricted region of a vessel). At the deployment cite, the sheath is retracted thereby releasing the stent. Once released, the stent self-expands to the deployed diameter.

FIG. 8 shows another stent 510 that is another embodiment of the present invention. The stent 510 is shown in a configuration corresponding to the stent when the stent has been initially fabricated from a tube (i.e., before the stent has been compressed on a catheter). Similar to the previous embodiments, the stent is shown longitudinally split and laid flat for ease of explanation. The stent includes 10 circumferential support structures CS1-CS10 spaced-apart along a longitudinal axis LA of the stent S10. Longitudinal struts 14 and apex portions 18 of the support structures CS1-CS10 define an undulating pattern that extends about the circumference of the stent 510. The undulating pattern defines a wave having a wavelength WL. Alternating pairs of the adjacent support structures are interconnected by circumferential connecting struts 16. For example, support structure pairs CS2 and CS3; CS4 and CS5; CS6 and CS7; and CS8 and CS9 are interconnected by circumferential connecting struts 16. Struts 16 interconnecting structure CS2 to structure CS3 and structure CS6 to structure CS7 extend downwardly, and struts 16 interconnecting structure CS4 to structure CS5 and structure CS8 to structure CS9 extend upwardly. By alternating the direction of extension, uniform expansion is facilitated.

Circumferential suction structures CS1 and CS2; CS3 and CS4; CS5 and CS6; CS7 and CS8; and CS9 and CS10 are not interconnected by circumferential connecting struts. Instead, these pairs are integrally connected to one another.

Referring again to FIG. 8, circumferential connecting struts 16 function to offset the apexes 18 of adjacent circumferential support structures relative to one another so that the apexes do not oppose one another. By offsetting the apex portions that face toward one another, the tips are prevented from contacting one another when in the expanded state thereby enhancing the stent's ability to conform to a lumen in which the stent is implanted. In the depicted embodiment, the circumferential connecting struts 16 have a length equal to about one and one half (i.e., 1.5) wavelengths WL. Preferably, the circumferential struts 16 have a length of at least one half (i.e., 0.5) the wavelength WL. The integrally connected pairs of circumferential support structures have apex portions 18 that oppose one another.

FIG. 9 shows a stent 610 that is another embodiment of the present invention. The stent 610 is shown in a configuration corresponding to the stent when the stent has been initially fabricated from a tube (i.e., before the stent has been compressed on a catheter). Similar to the previous embodiments, the stent is shown longitudinally split and laid flat for ease of explanation. The stent includes 10 circumferential support structures CS1-CS10 spaced-apart along a longitudinal axis LA of the stent 610. Longitudinal struts 14 and apex portions 18 of the support structures CS1-CS10 define an undulating pattern that extends about the circumference of the stent 510. Support structure pairs CS2 and CS3; CS3 and CS4; CS7 and CS8; and CS8 and CS9 are interconnected by circumferential connecting members 16. The remaining support structure pairs (i.e., pairs CS1 and CS2; CS4 and CS5; CS5 and CS6; CS6 and CS7; and CS9 and CS10) are interconnected by integrally.

In the embodiments of FIGS. 8 and 9, the circumferential connecting struts 16 are generally perpendicularly aligned relative to the apex portions 18. In other embodiments, the circumferential connecting struts 16 could be angled similar to the struts 416 of FIG. 7. In embodiments where the apex portions 18 are not longitudinally overlapped, the circumferential connecting struts could be angled in the opposite direction as compared to the struts 416 of FIG. 7.

While a preferred use for the inventive features disclosed in FIGS. 1-9 is in a self-expanding stent, the features also have benefits when used with non-self-expanding stents (e.g., balloon expandable stents made of a material such as stainless steel). Also, while FIGS. 1-9 illustrate a preferred geometry for practicing the present invention, the technique for avoiding opposing longitudinal members coming in direct contact by varying the offset positions of the struts and apex positions in a stent is also applicable to stents having other geometries, shapes, or strut patterns.

From the foregoing, the present invention has been shown in a preferred embodiment. Modifications and equivalents are intended to be included within the scope of the appended claims.

What is claimed is:

1. A stent comprising:
   a stent body expandable between an un-deployed orientation and a deployed orientation, the stent body having a circumference and a longitudinal axis extending between first and second open ends,
   the stent body having a plurality of circumferential support structures which extend generally about the circumference of the stent, each circumferential support structure including longitudinal struts interconnected at apex portions to define an undulating pattern; and
   a plurality of connecting struts interconnecting at least some of the adjacent circumferential support structures, at least one of the connecting struts having a uniform width along substantially an entire length of the respective at least one connecting strut, wherein the uniform width is at least twice as great as a width of at least one of the longitudinal struts.

2. The stent of claim 1, wherein the uniform width of the at least one of the connecting struts is at least five times as great as the width of the least one of the longitudinal struts.

3. The stent of claim 1, wherein each connecting strut has a width greater than the width of each longitudinal strut.

4. The stent of claim 1, wherein at least some of the connecting struts are dimensioned to connect select apex portions of adjacent circumferential support structures, the select apex portions circumferentially offset with respect to each other.

5. The stent of claim 4, wherein the connecting struts are substantially linear.

6. The stent of claim 5, wherein the connecting struts are dimensioned to extend perpendicular to the longitudinal axis of the stent body.

7. The stent of claim 5, wherein the connecting struts are dimensioned to extend in oblique relation to the longitudinal axis of the stent body.

8. The stent of claim 4, wherein the select apex portions of adjacent circumferential support structures are configured to longitudinally overlap when in the un-deployed orientation.

9. The stent of claim 1, wherein each circumferential support structure includes pairs of longitudinal struts alternating with single longitudinal struts.

10. The stent of claim 9, wherein the pairs of longitudinal struts are longer than the single longitudinal struts.

11. The stent of claim 9, wherein the pairs of longer longitudinal struts are interconnected by the connecting struts.

12. A stent comprising:
   a stent body expandable between an un-deployed orientation and a deployed orientation, the stent body having a circumference and a longitudinal axis extending between first and second open ends,
   the stent body having a plurality of circumferential support structures which extend generally about the circumference of the stent, each circumferential support structure including longitudinal struts interconnected at apex portions to define an undulating pattern,
   at least some of the apex portions of adjacent circumferential support structures being configured to longitudinally overlap when in the un-deployed orientation thus providing longitudinal overlap; and
   a plurality of connecting struts interconnecting at least some of the adjacent circumferential support structures, the connecting struts extending generally circumferentially between the apex portions that longitudinally overlap, the connecting struts each defining a uniform width along substantially an entire respective length of each respective connecting strut, wherein the uniform width is at least twice as great as a width defined by at least one of the longitudinal struts.

13. The stent of claim 12, wherein the connecting struts extending between the apex portions that longitudinally overlap are angled at an oblique angle with respect to the circumference of the stent body.

14. The stent of claim 12, wherein the connecting struts extending between the apex portions that longitudinally overlap are generally perpendicular to the longitudinal axis of the stent body.

15. The stent of claim 12, wherein the uniform width defined by each connecting strut is at least five times as great as the width defined by the least one of the longitudinal struts.

* * * * *